Aug. 23, 1966 C. PALMER Plant Pat. 2,665
PEACH TREE
Filed March 21, 1963
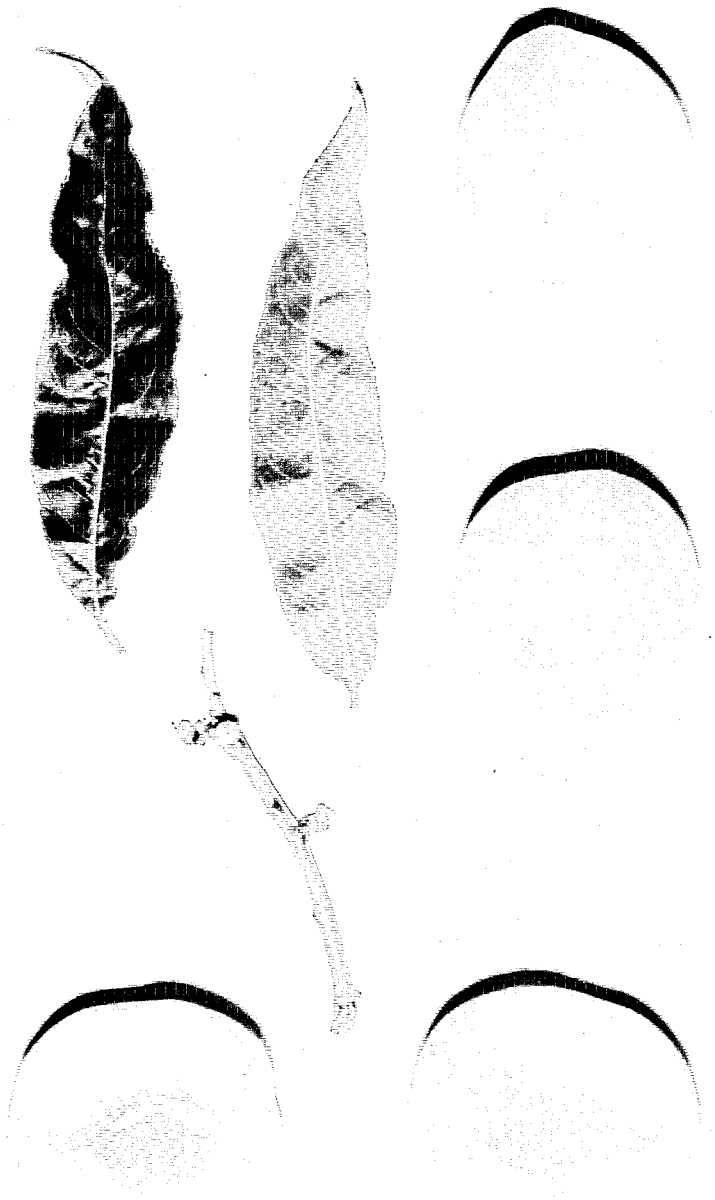
Conwin Palmer
Inventor United States Patent Office Plant Pat. 2,665
Patented August 23, 1966

2,665
PEACH TREE

Corwin Palmer, Rte. 4, Box 232, Montrose, Colo.

Filed Mar. 21, 1963, Ser. No. 267,895
1 Claim. (Cl. Plt.—42)

This invention relates to a novel variety of freestone white peach which is a seedling of unknown origin. This seedling was discovered eight (8) years ago. The fruit of this new variety favors the wild peach in coloration, and is the size of the Elberta. This peach is very juicy, sweet and firm—the flavor is very distinct and new. It is free of tannin, the acidity is definitely lower than the standard Elberta and the bitterness is much less than the standard Elberta. Its sweetness is definitely better than the Polly or Carmen. Its flesh is of a very fine texture and is not stringy. This is a very desirable tasting peach. The seed (pit) and flesh surrounding the pit are a deep red. Skin coloration is distinct, being a dull, cherry red mottled with darker oxblood red on one side, about one-third, and the other two-thirds is a cream color. It is very good as a canned fruit; requires less sweetening than most peaches. It ripens between late August and the first week of September. It does not have much fuzz. The blossoms are single and are as large as a half dollar. They are dark red in color; the last for several days before fading. The tree is resistant to heat, cold and disease. In the eight years that the petitioner has grown this peach it has withstood high temperatures of 98 to 100 degrees Fahrenheit and low temperatures of minus 12.5 degrees Fahrenheit in December 1961 and minus 24 degrees Fahrenheit on January 13, 1963, and has not been afflicted by blight, mildew or mosaic. I have asexually reproduced this tree by budding, and it adheres to new stock easily and propagates true to variety. The State University of Colorado Experiment Station at Austin, Colorado ran sugar tests on this peach and found it ran 16%. This test result was based upon samples from several of these peaches. Records of the State University of Colorado Experiment Station at Austin, Colorado, for the year and season corresponding to the year and season in which the tests on this peach were taken resulting in the above findings show the average sugar content of the standard Elberta and the July Elberta tested by them during this period was 12.9 and 13.0 respectively. All peaches were ripe when tested. This new variety of peach was discovered in a cultivated area, Montrose, Colorado, and not in an uncultivated state.

Tree: Medium to smallish in size; moderately vigorous; vase shaped; moderately productive; annual bearer.

*Trunk.*—Medium diameter; structurally strong; bark surface quite roughened in older trees.

*Branches.*—Medium diameter; sturdy, not willowy. Carry fruit load well. Bark tends to roughen on older trees; smooth on young wood. Lenticels are few and indistinct, small, color—medium green shading to olive brown, and becoming purple brown in sun exposed regions.

*Leaves.*—Size, medium to large, 4″ to 6″ long, about 1⅛″ to 1¼″ in width. Medium thickness. Lanceolate and acute at apex. Wavy; broadly acute at base. Leaf blades flat to slightly wavy. Leaf margin finely serrated. Color medium green. Petiole is quite short, ⅜″ to ½″; medium thickness. Glands are medium to small, 2 to 3 in number, globose and alternate. Stipules short, dehisce early. Two and three additional leaflets common, 2½ to 3 inches long.

*Flower buds.*—Large, rounded, smooth. Bud scales glabrous. Bloom about the same time as Elberta. Flowers are large and showy; dark red.

Fruit: Stage of maturity when described—firm ripe, September 10, 1964 (season later than normal).

*Size.*—Generally uniform, medium size: 2⅛″ to 2⅜″, axial diameter, transverse in the suture plane 2 1/16″ to 2¼″. At right angles to suture plane 2″ to 2 5/16″.

*Form.*—Slightly variable; oblong to round-ovate and slightly compressed at distal end (apex) in the suture plane; faintly tapered at apex. Suture fairly prominent, being nearly level with the cheeks at the base, and becoming broader and raised towards apex; faint line running full length of suture. apex flattened, with pistil or apex point short and often obscure, with slight depression before and after pistil point along suture line. The pistill point lacking in prominence, often with black point on slightly raised cross ridge. The base is flattened with stem cavity medium broad (18 mm.); moderately deep (13 mm.), rounded to slightly compressed in suture plane and somewhat irregular along basal edge. The dorsal edge (opposite suture edge) is full from bottom to near apex; broad and moderately flattened except for slight depression at apex to form shallow lipping. The stem is from 7 to 12 mm. long; about 4 mm. in diameter. Fruit adherence to stem is medium to strong. Skin is medium to thin, moderately tender; separates from flesh readily; free from cracking. Ground color greenish cream to cream white; mostly washed and blushed with a dull cherry red (listed as strong purple red 10RP 4/12 to 5/12 according to the Nickerson Color Fan, based on Munsell Hues), and streaked and mottled with darker oxblood red (dark red or 2.5R 3/7 by Nickerson Color Fan). Balance of ground color is stippled or spotted with numerous reddish dots (strong red 5R 4/12, Nickerson Color Fan). Pubescence (fuzz) is relatively free, light, short, and compressed to fruit; gives a smooth appearance and feel.

*Flesh.*—Color white, with streaks of medium to dark red piercing the flesh close to the stone.. The surface of pit cavity is stippled and dotted with red (geranium lake). Texture is medium to firm; fine melting; fibres are fine and tender; juice abundant; moderately sweet; very sweet when fully ripe. Ripens uniformally over entire fruit. Fruit usually ripens uniformally on tree. Flavor is mild, subacid, delicate—good balance between sugar and acids. Aroma not pronounced. Quality as dessert or canned is good to very good.

*Stone.*—Moderately free. Size medium to small, 1¼″ to 1⅜″ in length. Breadth is 9/16″ to ⅞″. Thickness, ⅜″ to 7/16″, form is elliptical, with medium wide base and tapered wedge, cuneate apex. The hilum at base is small and narrow. Sides equal to slightly unequal, strongly curved on both sides. Surface moderately smooth with shallow furrows and indentations, no prominent markings. Dorsal and ventral edge: Each is uniform with shallow, fine groove from base to apex. Color of stone is medium brown with red along both ventral and dorsal edge. No tendency of stone to split.

*Uses.*—Roadside and home use, dessert and canning.

*Keeping quality.*—Short to medium.

I would like to call the peach "Palmer White." See colored drawing.

I claim:

A new and distinct variety of peach tree of the white-flesh, freestone class, substantially as herein shown and described, particularly characterized as to novelty by the unique combination of the coloration of the wild peach and the size of the Elberta, by its large and showy blossoms and by the fine texture, abundance of juice, firmness, relative lack of pubescence and the delicate, desirable flavor of its fruit.

No references cited.

ANTONIO F. GUIDA, *Acting Primary Examiner.*

T. GRAHAM CRAVER, A. G. STONE, *Examiners.*

R. E. BAGWILL, *Assistant Examiner.*